United States Patent [19]

Ford et al.

[11] Patent Number: 4,503,253

[45] Date of Patent: Mar. 5, 1985

[54] PRODUCTION OF NONCYCLIC POLYALKYENE POLYAMINES

[75] Inventors: Michael E. Ford, Center Valley; Thomas A. Johnson, Orefield, both of Pa.

[73] Assignee: Air Products and Chemicals, Inc., Allentown, Pa.

[21] Appl. No.: 587,435

[22] Filed: Mar. 8, 1984

[51] Int. Cl.$^3$ ............................................. C07C 85/06
[52] U.S. Cl. .................................................... 564/479
[58] Field of Search ........................................ 564/479

[56] References Cited

U.S. PATENT DOCUMENTS

| | | | |
|---|---|---|---|
| 3,714,259 | 1/1973 | Lichtenwalter et al. | 260/583 |
| 3,766,184 | 10/1973 | Johansson et al. | 260/268 |
| 4,036,881 | 7/1977 | Brennan et al. | 260/583 |
| 4,044,053 | 8/1977 | Brennan et al. | 260/583 |
| 4,103,087 | 7/1978 | Brennan | 564/479 X |
| 4,314,083 | 2/1982 | Ford et al. | 564/479 |
| 4,324,917 | 4/1982 | McConnell | 564/479 |
| 4,394,524 | 7/1983 | Ford et al. | 564/479 |
| 4,448,997 | 5/1984 | Brennan | 564/479 |

*Primary Examiner*—Paul F. Shaver
*Attorney, Agent, or Firm*—Russell L. Brewer; E. Eugene Innis; James C. Simmons

[57] ABSTRACT

A process for preparing predominantly noncyclic polyalkylene polyamine compounds is disclosed wherein an alkanolamine compound is reacted with an alkyleneamine compound optionally with ammonia or a primary or secondary amine in the presence of a catalytically effective amount of a catalyst containing phosphoric acid incorporated onto an inert support at a temperature from about 175° to 400° C. under a pressure sufficient to maintain a substantial amount of the ammonia or amine in the reaction zone.

20 Claims, No Drawings

: 1

PRODUCTION OF NONCYCLIC POLYALKYENE POLYAMINES

TECHNICAL FIELD

This invention relates to the preparation of polyalkylene polyamines, particularly noncyclic polyalkylene polyamines.

BACKGROUND OF THE INVENTION

Low molecular weight polyethylene polyamines are used in a wide variety of applications such as corrosion inhibitors, fabric softeners, lubricating oil additives, fungicides and many others. Despite the utility of polyethylene polyamines, they are currently obtained only as by-products of ethylenediamine manufactured by the reaction of ethylene dichloride with excess ammonia. Since the polyamines are by-products of ethylenediamine preparation, the supply and quality of available polyethylene polyamines are often variable. Generally, high yields of cyclic polyethylene polyamines, e.g., piperazine, aminoethylpiperazine and the like, are produced although it is the noncyclic polyamines such as diethylenetriamine, linear and branched triethylenetetramine and higher homologs that are commercially desirable. Moreover, since sodium chloride is co-produced in large quantities, separation of the products from the sodium chloride and the handling and disposal of this corrosive inorganic salt require special measures.

The prior art discloses various attempts to circumvent these difficulties and to provide controllable efficient routes to polyethylene polyamines:

U.S. Pat. No. 3,714,259 discloses the preparation of linear polyethylene amines by contacting ethanolamine with ethylenediamine compound in the presence of hydrogen and a hydrogenation catalyst. An example of a hydrogenation catalyst is nickel containing copper and chromium components. Significant amounts of water are included in the feedstock, namely 25–50 wt% based on the combined starting ethylenediamine and monoethanolamine.

U.S. Pat. No. 3,766,184 discloses the reductive amination of monoethanolamine by a metallic catalyst of iron and nickel and/or cobalt in the presence of hydrogen.

U.S. Pat. No. 4,036,881 discloses the preparation of polyalkylene polyamines by reacting an alkanolamine with an alkyleneamine compound in the presence of a phosphorus containing substance selected from the group consisting of acidic metal phosphates, phosphoric acid compounds and anhydrides and the phosphate esters.

U.S. Pat. No. 4,044,053 is somewhat similar to the '881 patent except that the alkyleneamine compound is present in an excess amount and a diol is used in place of the alkanolamine.

U.S. Pat. No. 4,314,083 discloses a process for selectively preparing predominantly noncyclic polyalkylene polyamines by reacting an alkanolamine with an alkyleneamine compound in the presence of a salt of a nitrogen or sulfur containing substance or the corresponding acid.

U.S. Pat. No. 4,324,917 discloses ion exchange resins containing phosphonic acid functionality as catalysts for the production of polyethylene polyamines by alkylation of alkyleneamines such as ethylenediamine with alkanolamines such as monoethanolamine.

It can be seen that the prior art requires a source of preformed ethylenediamine for reaction with monoethanolamine to produce polyethylene amines. There must be a sufficient quantity of ethylenediamine present initially in the reaction mixture or a sufficient quantity continuously added to the reaction mixture in the prior art processes. Thus, production of polyethylene amines requires preparation of substantial quantities of both monoethanolamine, the alkylating agent, and ethylenediamine, the aminating agent, in separate steps and subsequent co-polymerization of the monomers to provide polyethylene polyamines. Prior art routes to polyethylene polyamines are therefore limited by their dependence on a sufficient supply of preformed ethylenediamine compared to monoethanolamine in the reactions.

SUMMARY OF THE INVENTION

It has been found that noncyclic, or linear and branched, polyalkylene polyamines are produced in good yield by reacting an alkanolamine compound with an alkyleneamine compound in the presence of a catalytically effective amount of a phosphoric acid incorporated on an inert support at a temperature sufficient to effect reaction between the alkanolamine compound and the alkyleneamine compound under a pressure sufficient to maintain a substantial amount of the amine in the reaction zone.

As an advantage of the invention, the process provides predominantly noncyclic polyalkylene polyamines from mixtures of ammonia, alkanolamine and an alkyleneamine with relatively little or no net consumption of the alkyleneamine. As an additional advantage, varying amounts of polyamine products may be recycled in place of the small amounts of alkyleneamine that may be consumed in polyamine formation. In this way, product slate flexibility may be increased by homologation of intermediate polyamines, such as diethylenetriamine and piperazine, to higher polyamines, such as the isomeric noncyclic and cyclic triethylenetetramine and tetraethylenepentamines. In either embodiment, compared to the alkanolamine compound, the process does not require a significant supply of an alkyleneamine as a feedstock for making the polyalkylene polyamines. By the process of the invention a substantially constant concentration of alkyleneamine may be maintained during polyamine formation.

Predominantly noncyclic polyalkylene polyamines means greater than about 50 wt% of linear and branched polyalkylene polyamines in the total polyamine product.

In the preferred embodiment, mixtures of ethylenediamine, monoethanolamine and ammonia are converted to predominantly noncyclic polyamines by a process in which a substantially constant concentration of ethylenediamine is maintained during polyamine formation. Appropriate choice of key process variables, particularly feed compositions, catalyst level in batch operation or space velocity in continuous operation, temperature and pressure, allows consumption of ethylenediamine by polyamine formation to be substantially balanced with production of ethylenediamine by amination of monoethanolamine. The process affords predominantly noncyclic polyethylene polyamines in high conversion and selectivity with less alkyleneamine consumption than would be possible in the absence of ammonia.

As a further advantage the use of supported phosphoric acids as catalysts avoids problems associated with co-production of stoichiometric quantities of an inorganic salt.

Moreover, phosphoric acids on inert supports are dimensionally stable, i.e., they do not swell and agglomerate during polyamine formation as may Group IIIB metal acidic phosphates. Consequently, supported phosphoric acids are preferred catalysts for continuous, large-scale polyalkylenepolyamine production.

Furthermore, in contrast to many Group IA acid phosphates, supported phosphoric acids are insoluble in the reaction medium. Thus, under conditions for operation of this process, supported phosphoric acids are insoluble solids that are easily localized in a fixed bed or continuous stirred tank reactor. Isolation of polyamine products, particularly in continuous processes, is therefore readily accomplished.

As an additional advantage a wide range of noncyclic polyamines is produced without the necessity of including an inert diluent in the feed and removing it from the reaction product.

DETAILED DESCRIPTION OF THE INVENTION

The invention relates to a process for synthesizing predominantly noncyclic polyalkylene polyamines, preferably linear and branched polyethylene polyamines such as diethylenetriamine and higher homologs. In the process an alkyleneamine having two amino groups and, preferably, an unbranched alkylene moiety, such as ethylenediamine, is reacted with an alkanolamine having a primary or secondary hydroxy moiety and an amino group. Preferably, the alkanolamine has an unbranched alkyleneamine moiety.

The alkanolamine compounds which are used in practicing the process include those represented by the general formula:

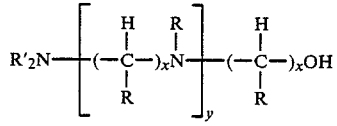

where R is hydrogen or a lower alkyl ($C_1$–$C_4$) radical, R' is hydrogen or an alkyl ($C_1$–$C_{25}$) radical, x is a number from 2 to 6, and y is a number from 0 to 3. Exemplary of suitable alkyl radicals are the lower ($C_1$–$C_4$) alkyls, such as methyl, ethyl and butyl, and higher alkyls such as octyl, decyl and octadecyl. Methyl is the preferred lower alkyl radical. However, it is preferred that R and R' be hydrogen. Thus the alkanolamine would contain a primary amino group. Examples of alkanolamine compounds that can be used are the ethanolamines, isomeric propanolamines, N-(2-aminoethyl)ethanolamine, N-methylethanolamine, N,N-dimethylethanolamine, N,N,N'-trimethylaminoethylethanolamine and the like.

The alkyleneamine reactants that can be used in practicing the process are represented by the general formula:

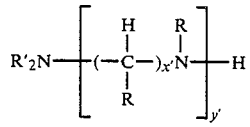

where R is a hydrogen or lower alkyl ($C_1$–$C_4$) radical, R' is hydrogen or an alkyl ($C_1$–$C_{25}$) radical, x' is a number from 2 to 6, and y' is a number from 1 to 4. Exemplary of suitable alkyl radicals are the lower ($C_1$–$C_4$) alkyls, such as methyl, ethyl and butyl, and higher alkyls such as octyl, decyl and octadecyl. It is preferred that R and R' be hydrogen. The preferred lower alkyl radical is methyl. Examples of alkyleneamine compounds suited for the reaction include 1,3-propylenediamine, N-methylpropylenediamine, 1,2-propylenediamine, diethylenetriamine, N,N,N'-trimethyldiethylenetriamine, noncyclic isomers of triethylenetetramine, noncyclic isomers of tetraethylenepentamine, N-methylethylenediamine, N,N-dimethylethylenediamine and ethylenediamine which is the preferred alkyleneamine compound.

Ammonia and primary and secondary amines which can be used in the process along with the alkyleneamine and these can be represented by the general formula

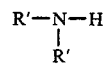

where R' is hydrogen or an alkyl ($C_1$–$C_{25}$) radical, preferably a lower alkyl ($C_1$–$C_4$) radical, such as methyl or ethyl. Proposed amine feedstocks include monomethylamine, dimethylamine, monoethylamine, diethylamine, octylamine and octadecylamine.

Noncyclic polyalkylene polyamines that are produced by the reaction of an alkyleneamine and an alkanolamine are represented by the general formula:

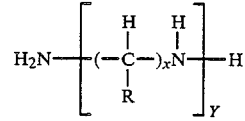

where R is hydrogen or a lower alkyl ($C_1$–$C_4$) radical, preferably a methyl radical, X is a number from 2 to 6, Y is a number from 2 to 7, and X may vary for a given value of Y. Examples of such noncyclic polyalkylene polyamines that are produced include dipropylenetriamine, tributylenetetramine, di(2-methylethylene)triamine, tri(2-methylethylene)tetramine, N-(2-aminoethyl)-1,3-propylenediamine, diethylenetriamine, and the noncyclic isomers of triethylenetetramine and tetraethylenepentamine.

Use of secondary amines instead of ammonia would lead to polyamines containing terminal dialkylamino groups. Alternatively, use of primary amines instead of ammonia would lead to polyamines which contain randomly distributed monoalkylamino groups.

One embodiment of the invention comprises a continuous process for preparing predominantly noncyclic polyalkylene polyamines by (a) adding a charge comprising an alkanolamine compound to a reaction zone containing an alkyleneamine compound optionally with ammonia or a primary or secondary amine and a catalytically effective amount of phosphoric acid on an inert support at a temperature sufficient to effect a reaction among the ammonia or amine, the alkanolamine compound and the alkyleneamine compound under a pressure sufficient to maintain a substantial amount of the ammonia or amine in the reaction zone to produce a reaction product stream containing ammonia or primary or secondary amine, alkanolamine compound, alkyleneamine compound and polyalkylene polyamines, and (b) withdrawing the product stream from the reaction zone and separating it to provide a polyalkylene polyamine stream and ammonia or the primary or secondary amine, alkanolamine compound and alkylene compound which are recycled to the reaction zone.

The invention can also be viewed as a method for substantially reducing the amount of alkyleneamine compound in the feed to the reaction zone in a continuous process for the preparation of predominantly noncyclic polyalkylene polyamines which continuous process comprises continuously adding a feed containing an alkanolamine compound and an alkyleneamine compound to a reaction zone containing a catalyst to yield a product stream comprising the polyamines, alkanolamine compound and alkyleneamine compound, separating the desired polyamines from the product stream and recycling the alkanolamine and alkyleneamine compounds to the reaction zone. The method of the invention would comprise (a) adding ammonia or a primary or secondary alkylamine to the feed to the reaction zone,
(b) using a catalytically effective amount of a supported phosphoric acid as the catalyst, and
(c) effecting the reaction under a pressure sufficient to maintain a substantial amount of the ammonia or amine in the reaction zone.

To practice such a continuous process to make dialkylamino end-capped polyamines the alkanolamine compound must be reacted with the dialkylamine in the presence of an N,N-dialkylalkylenediamine, i.e., an alkyleneamine compound with one primary amino group and one tertiary amino group.

Similarly, when a monoalkylamine is substituted for ammonia, the alkyleneamine must have one primary amino group and one secondary amino group, e.g., N-methyl ethylenediamine would be used to make randomly mono-methyl substituted polyamines.

Other possibilities include the preparation of predominantly noncyclic polyamines derived from N-alkylalkanolamines. For example, the reaction of ammonia with N-methyl ethanolamine and N-methyl ethylenediamine also generates randomly methylated, although more highly methyl substituted, polyamines. However, if monomethylamine is substituted for ammonia, the polyamine becomes 100% methyl substituted, i.e., every nitrogen contains one methyl group. It should be apparent that in this and the former cases, the alkyleneamine whose concentration is to be maintained substantially constant is that which is formed by the reaction of the alkylamine or ammonia with the alkanolamine.

The catalysts which are suited for practicing the process of the invention are phosphorus-containing substances, i.e. phosphorous or phosphoric acid on an inert support, e.g., silica. Unlike many prior art catalyst systems, this is a heterogeneous catalyst system as opposed to a homogeneous catalyst. This feature permits easy recovery of the catalyst from the reaction mixture and permits the use of fixed bed reactors. Inert supports which can be utilized include silica, alumina, carbon silica-alumina clays and molecular sieves, e.g. aluminosilicates.

The weight of phosphoric acid to support is variable and its optimum level will depend upon the reactants and operating conditions. Typically, the weight of phosphoric acid to support is from 1 to 85%.

The quantity of phosphoric acid in the catalyst used for polyamine production is somewhat empirical and can vary widely depending upon the reactivity of the catalyst and the reactivity of the reactants present. An effective amount of catalyst is used; in other words, an amount which causes reaction among ammonia, the alkyleneamine, and the alkanolamine to yield noncyclic polyamine products at the temperature and pressure used. Usually though, the amount used to provide a catalytic effect for batch reactions ranges from about 0.1 to 25 mole % based on the total amount of alkyleneamine and alkanolamine present in the reaction zone, and preferably is an amount of about 0.1 to 15 mole %. For continuous reactions, e.g., in a packed bed tubular reactor, the amount of catalyst used is adjusted to permit operation at liquid hourly space velocities (based on alkanolamine and alkyleneamine) from about 0.05 hr.$^{-1}$ to 50.0 hr.$^{-1}$. Within these ranges, though, the level of catalyst is empirical and is adjusted depending on the product slate desired.

In the preparation of noncyclic polyalkylene polyamines, and preferably the noncyclic polyethylene polyamines, the reaction is maintained at a temperature from about 175° C. to about 400° C., and preferably is carried out between 210° C. and 350° C. to obtain a practical rate of polyamine production without generation of excess levels of high molecular weight products.

Although the reactions can be carried out in the batch mode, they are preferably operated in continuous processes, for example operation of a continuous stirred tank reactor or a packed bed reactor. The reaction is allowed to proceed until a desired conversion is obtained or the reaction is complete. Normally the reaction is carried out within about 0.5 to 5 hours in the batch mode or space velocities (based on alkanolamine and alkyleneamine components) of 0.05 to 50.0 hr.$^{-1}$ in a continuous mode for practical levels of polyamine production. For continuous reactions, such as those carried out at controlled pressures in a fixed bed reactor or in a continuous stirred tank reactor, the pressure utilized for the reaction may range from 1 to 150 atm, typically 5-150 atm—but preferably is that pressure which is sufficient to maintain a substantial amount of the ammonia or amine in the reaction zone.

Failure to retain a substantial amount of the ammonia or amine in the reaction zone in either batch or continuous process will lead to high net consumption of alkyleneamine, owing to low production of the alkyleneamine by the amination of the alkanolamine. Reaction pressure must be sufficiently high, preferably at least 75 psig, to maintain a significant portion of the ammonia or lower alkyl amine in the reaction zone. Preferred reaction times and catalyst levels depend on catalyst reactivity and are adjusted empirically. Thus, for example, relatively lower catalyst incorporations and shorter reaction times are preferred for the production of polyamines with more reactive catalysts.

Generally, the mole ratio of alkyleneamine compound to alkanolamine compound may range from about 0.5:1 to 12:1, and preferably is about 0.75:1 to 10:1. It is advantageous in carrying out the process that the proportion of alkyleneamine compound to alkanolamine compound be in a molar ratio of at least about 0.75:1 in order to obtain the advantage of the invention in which a substantially constant concentration of alkyleneamine is maintained during polyamine formation. When the alkyleneamine compound approaches a 0.75:1 molar ratio with the alkanolamine, or falls below that level, the alkanolamine may have a tendency to form the cyclic amine compositions although the addition of ammonia or an amine as a reactant greatly diminishes this tendency.

With respect to the amount of ammonia or amine present in the reaction mixture the molar quantity of ammonia or amine may range from about 0.25:1 to 15:1 with respect to total alkyleneamine compound and alkanolamine compound, and preferably is about 0.75:1 to 10:1 although large excess quantities of ammonia or amine can be used.

It is preferred when reacting ethylenediamine (EDA) and monoethanolamine (MEA) with ammonia that the mole ratios be in a range of 0.75-10:0.5-2:0.10-20 (EDA:MEA:NH$_3$).

Recovery of the polyalkylene polyamines from the reaction mixture can be accomplished by conventional techniques, these techniques generally involving a distillation. Often a small amount of a salt, such as the one used as the catalytic material, is added to the polyalkylene polyamine separation purification as described in U.S. Pat. No. 3,755,447.

The following examples which illustrate the nature of the process are not intended to limit the scope of the invention. In each example the reactions were carried out under the indicated conditions in a fixed bed packed reactor. In a fixed bed packed reactor the back pressure regulator was set within the range 200-300 psig.

EXAMPLE 1

Phosphoric acid on silica (34% by weight; 5 cm$^3$ of $-12$ to $-18$ mesh particles) mixed with 5 cm$^3$ of crushed Vicor ($-12$ to $-18$ mesh) was charged to a fixed bed tubular reactor. The reactor was heated to 255° in an insulated oven. A mixture of ethylenediamine, monoethanolamine, and ammonia (mole ratio of ethylenediamine:monoethanolamine:ammonia is 2:1:11) was passed over the catalyst (LHSV=1.5 hr$^{-1}$, based on ethylenediamine and monoethanolamine at 300 psig. Analysis of the cooled reaction product by gas liquid chromatography indicated substantial production of predominantly noncyclic polyamines (see Tables 1 and 2). Other examples which follow the tables are also reported in these tables to facilitate review.

EXAMPLE 2A-F

Phosphoric acid on silica (34% by weight; 5 cm$^3$ of $-12$ to $-18$ mesh particles) was charged to a fixed bed tubular reactor. A mixture of ethylenediamine, monoethanolamine, and ammonia (mole ratio of ethylenediamine:monoethanolamine:ammonia is 2:1:8) was passed over the catalyst (LHSV=2.3 hr.$^{-1}$, based on ethylenediamine and monoethanolamine) at 245 psig and 250°. This reaction was operated continuously for 502 hours to evaluate catalyst life. Analysis of cooled reaction products sampled at the times indicated in Table 1 showed not only substantial production of predominantly noncyclic polyamines, but also that catalyst reactivity and selectivity did not change significantly during this run (see Tables 1 and 2 for additional detail).

EXAMPLE 3

The procedure of Example 1 was repeated with a 4:1:12 molar feed ratio of ethylenediamine:monoethanolamine:ammonia (LHSV=2.0 hr.$^{-1}$, based on ethylenediamine and monoethanolamine) at 260° C. and 250 psig. Analysis of the cooled reaction product indicated substantial production of predominantly noncyclic polyamines (see Tables 1 and 2).

EXAMPLE 4

The procedure of Example 3 was repeated with a 4:1:8 molar feed ratio of ethylenediamine:monoethanolamine:ammonia (LHSV=2.7 hr.$^{-1}$, based on ethylenediamine and monoethanolamine). Analysis of the cooled reaction product indicated substantial production of predominantly noncyclic polyamines (see Tables 1 and 2).

EXAMPLE 5

The procedure of Example 3 was repeated at 240° C. Analysis of the cooled reaction product indicated substantial production of predominantly noncyclic polyamines (see Tables 1 and 2).

EVALUATION OF DURABILITY AND DIMENSIONAL STABILITY OF SUPPORTED PHOSPHORIC ACID POLYAMINES CATALYST

EXAMPLE 6

Phosphoric acid on silica (34% by weight; 5 cm$^3$ of $-12$ and $-18$ mesh particles) were confined within a 5 cm$^3$ volume established between a fixed screen at the top of the reactor and a support at the bottom of the reactor. A mixture of ethylenediamine:monoethanolamine:ammonia (mole ratio of ethylenediamine:monoethanolamine:ammonia was 2:1:8) was passed over the catalyst (LHSV=2.1 hr.$^{-1}$, based on ethylenediamine and monoethanolamine) at 250 psig and 250° C. The screen confines the catalyst charge to its initial 5 cm$^3$ volume. Constraining the catalyst in this fashion permits evaluation of swelling and/or agglomeration. High differential pressures across the catalyst bed and ultimate reactor plugging indicate undesirable catalyst behavior. After 91.5 hours of continuous operation, analysis of a sample of the cooled reaction product indicated substantial production of predominantly noncyclic polyamines) (see Tables 1 and 2). Moreover, the pressure drop across the catalyst bed during this evaluation was ≦0.1 psig. Immediately after completion of this example, Example 7 was carried out with the catalyst charge.

COMPARATIVE EXAMPLE 6A

The procedure of Example 6 was repeated with substitution of a mixture of lanthanum acid phosphate (5 cm$^3$ of $-12$ to $-18$ mesh particles) and α-alumina (5 cm$^3$ of $-12$ to $-18$ mesh particles; α-alumina is included to separate the particles of lanthanum acid phosphate) confined to a 10 cm$^3$ bed. After 72.6 hours of continuous operation, analysis of a sample of the cooled reaction product indicated substantial production of predominantly noncyclic polyamines (see Tables 1 and 2). During this period, the pressure drop across the reactor rose to 1.0 psig. Although conversion and selectivity were comparable to those obtained in Example 6, the catalyst/alumina mixture had fused into a solid mass. Prior to the testing of phosphoric acid on silica, the lanthanum acid phosphate catalyst had been the preferred systems with respect to agglomeration.

COMPARATIVE EXAMPLE 6B

The procedure of Comparative Example 6A was repeated with LHSV=2.4 hr.$^{-1}$, based on ethylenediamine and monoethanolamine. After 21.6 hours of continuous operation, analysis of a sample of the cooled reaction product indicated substantial production of predominantly noncyclic polyamines (see Tables 1 and 2). During the period, the pressure drop across the reactor rose to 9.0 psig, and the catalyst/alumina mixture had fused into a solid mass.

EXAMPLE 7

The procedure of Example 6 was repeated at 240° C. After 47.5 hours of continuous operation, analysis of a sample of the cooled reaction product indicated substantial production of predominantly noncyclic polyamines (see Tables 1 and 2). During this period, the pressure drop across the catalyst bed was $\leq 0.1$ psig. Example 8 was done with this catalyst charge immediately after completion of Example 7.

COMPARATIVE EXAMPLE 7

The procedure of Comparative Example 6A was repeated at 240° C. After 71.8 hours of continuous operation, analysis of a sample of the cooled reaction product indicated substantial production of predominantly noncyclic polyamines (see Tables 1 and 2). During this period, the pressure drop across the catalyst bed rose to 13.0 psig, and the catalyst had fused into a solid mass.

EXAMPLE 8

The procedure of Example 6 was repeated at 2:1:4 molar feed of ethylenediamine:monoethanolamine:ammonia (LHSV=3.0 hr.$^{-1}$, based on ethylenediamine and monoethanolamine). After 91.8 hours of continuous operation, analysis of a sample of the cooled reaction product indicated substantial production of predominantly noncyclic polyamines (see Tables 1 and 2). During this period, the pressure drop across the catalyst bed was $\leq 0.1$ psig owing to the consistant performance demonstrated by the supported phosphoric acid catalyst in Examples 6-8, this same catalyst charge was used for Examples 9-11 (q.v.).

COMPARATIVE EXAMPLE 8A

The procedure of Comparative Example 6A was repeated with a 2:1:4 molar feed ratio of ethylenediamine:monoethanolamine:ammonia (LHSV=2.6 hr.$^{-1}$, based on ethylenediamine and monoethanolamine). After 69.6 hours of continuous operation, analysis of a sample of the cooled reaction product indicated substantial production of predominantly noncyclic polyamines (see Tables 1 and 2). During this period, the pressure drop across the reactor rose to 2.0 psig, and the catalyst/alumina mixture fused into a solid mass.

COMPARATIVE EXAMPLE 8B

The procedure of Comparative Example 7A was repeated at 300 psig, with substitution of 10 cm$^3$ of lanthanum acid phosphate (−12 to −18 mesh) for the lanthanum acid phosphate/alumina mixture. After 2.5 hours of operation, the pressure drop across the catalyst bed rose to 10.0 psig, and flow through the reactor was blocked. Upon removal from the reactor, the catalyst had fused into a solid mass.

COMMENTS ON EXAMPLES 6-8

Comparable conversions and selectivities are obtained with phosphoric acid on silica and lanthanum and phosphate catalysts, with the exception of Comparative Examples 6B and 8B. In the latter cases, agglomeration and subsequent loss of surface area by lanthanum acid phosphate reduce the conversion of monoethanolamine to polyamines. However, facile aggregation of lanthanum acid phosphate poses a major obstacle to commercial polyamine production. As shown by Examples 6-8, this difficulty is surmounted by use of phosphoric acid on silica, which is stable under conditions of polyamine formation.

Examples 6-8 show that phosphoric acid on silica avoids problems associated with fusion of the lanthanum acid phosphate catalyst under moderate reaction conditions. To further explore the suitability of phosphoric acid on silica for polyamine production, reactions at lower temperatures were examined (Examples 9-11). Under the conditions of all of the following examples, attempts to provide comparative examples with lanthanum and phosphate resulted in rapid ($\leq 2$ hours of continuous operation) plugging of the reactor.

EXAMPLE 9

The procedure of Example 6 was repeated at 230° C. After 31.8 hours of continuous operation under these conditions, analysis of a sample of the cooled reaction product indicated substantial production of predominantly noncyclic polyamines (see Tables 1 and 2). During this period, the pressure drop across the catalyst bed was $\leq 0.1$ psig. Owing to the continued low pressure drop, the catalyst charge was not removed from the reactor. Example 10 was carried out immediately after completion of Example 9.

EXAMPLE 10

The procedure of Example 6 was carried out with a 2:1:4 molar feed ratio of ethylenediamine:monoethanolamine:ammonia at 240° C. After 147.9 hours of continuous operation under these conditions, analysis of a sample of the cooled reaction product indicated substantial production of predominantly noncyclic polyamines (see Tables 1 and 2). During this period, the pressure drop across the catalyst bed was $\leq 0.1$ psig. Example 11 was carried out immediately after completion of this example with the same catalyst charge.

EXAMPLE 11

The procedure of Example 10 was repeated at 230° C. After 90.6 hours of continuous operation, analysis of a sample of the cooled reaction product indicated substantial production of predominantly noncyclic polyamines (see Tables 1 and 2). During this period, the pressure drop across the catalyst bed was $\leq 0.1$ psig. Upon removal from the reactor, the catalyst used for Examples 6-12 (501.1 hours of continuous operation under all conditions) showed no signs of agglomeration or attrition.

COMMENTS ON EXAMPLES 9-11

Examples 9-11 show that predominantly noncyclic polyamines can be produced reliably with a supported phosphoric acid under conditions with which a lanthanum acid phosphate catalyst is inoperable. Conversion of monoethanolamine depends directly on reaction temperature (see Examples 10, 11). In addition, as the mole ratio of ammonia in the feed is decreased, selectivity to AEEA, a potentially valuable coproduct of this route to polyamines, increases (see Examples 9, 11).

It is readily apparent that the process of this invention provides predominantly noncyclic polyethylene polyamines in high conversion and selectivity from mixtures of ethylenediamine or a higher noncyclic polyethylene polyamine, monoethanolamine and ammonia. With inclusion of ammonia, significant amounts of monoethanolamine are converted to ethylenediamine and, by homologation of ethylenediamine, to higher noncyclic polyamines during polyamine formation. Consequently, although ethylenediamine or a higher alkyleneamine is present as a component of the reaction mixture, this process has minimal or no dependence on a source of the preformed alkyleneamine.

In contrast to the prior art, the process of this invention not only produces predominantly noncyclic polyamines but also minimizes or eliminates the need for preformed ethylenediamine. Unexpectedly, the inclusion of ammonia or amines in reactions of monoethanolamine and ethylenediamine allows efficient production of predominantly noncyclic polyamines from ethylenediamine and monoethanolamine and in situ regeneration of ethylenediamine by amination of monoethanolamine.

TABLE 1

| Example | Catalyst | LHSV $(hr^{-1})^a$ | Temp (°C.) | Press (psig) | Mole Ratio $(EDA/MELA/NH_3)^b$ | Conversion$^c$ (%)$^d$ | Selectivity$^c$ (NC)$^e$ | (AZEEA)$^f$ |
|---|---|---|---|---|---|---|---|---|
| 1 | 34% H$_3$PO$_4$ on Silica | 1.5 | 255 | 300 | 2/1/11 | 57 | 71 | 1 |
| 2A | 34% H$_3$PO$_4$ on Silica 42.5 hr | 2.3 | 250 | 245 | 2/1/8 | 40 | 69 | 2 |
| 2B | 34% H$_3$PO$_4$ on Silica 89.0 hr | 2.3 | 250 | 245 | 2/1/8 | 43 | 65 | 3 |
| 2C | 34% H$_3$PO$_4$ on Silica 119.5 hr | 2.3 | 250 | 245 | 2/1/8 | 42 | 65 | 2 |
| 2D | 34% H$_3$PO$_4$ on Silica 192.0 hr | 2.3 | 250 | 245 | 2/1/8 | 42 | 67 | 2 |
| 2E | 34% H$_3$PO$_4$ on Silica 291.5 hr | 2.3 | 250 | 245 | 2/1/8 | 40 | 69 | 2 |
| 2F | 34% H$_3$PO$_4$ on Silica 502.0 hr | 2.3 | 250 | 245 | 2/1/8 | 39 | 68 | 2 |
| 3 | 34% H$_3$PO$_4$ on Silica | 2.0 | 260 | 250 | 4/1/12 | 68 | 79 | 0 |
| 4 | 34% H$_3$PO$_4$ on Silica | 2.7 | 260 | 250 | 4/1/8 | 58 | 79 | 0 |
| 5 | 34% H$_3$PO$_4$ on Silica | 2.0 | 240 | 250 | 4/1/12 | 34 | 86 | 1 |
| 6 | 34% H$_3$PO$_4$ on Silica | 2.3 | 250 | 250 | 2/1/8 | 39 | 62 | 2 |
| Comparative 6A | Lanthanum Acid Phosphate/ Alumina | 2.1 | 250 | 250 | 2/1/8 | 36 | 72 | 3 |
| Comparative 6B | Lanthanum Acid Phosphate/ Alumina | 2.4 | 250 | 250 | 2/1/8 | 21 | 69 | 6 |
| 7 | 34% H$_3$PO$_4$ on Silica | 2.2 | 240 | 250 | 2/1/8 | 28 | 71 | 5 |
| Comparative 7 | Lanthanum Acid Phosphate/ Alumina | 2.0 | 240 | 250 | 2/1/8 | 29 | 75 | 5 |
| 8 | 34% H$_3$PO$_4$ on Silica | 3.0 | 250 | 250 | 2/1/4 | 33 | 72 | 5 |
| Comparative 8A | Lanthanum Acid Phosphate/ Alumina | 2.6 | 250 | 250 | 2/1/4 | 35 | 76 | 4 |
| Comparative 8B | Lanthanum Acid Phosphate | 2.6 | 250 | 250 | 2/1/4 | g | g | g |
| 9 | 34% H$_3$PO$_4$ on Silica | 2.2 | 230 | 248 | 2/1/8 | 19 | 69 | 8 |
| 10 | 34% H$_3$PO$_4$ on Silica | 2.8 | 240 | 253 | 2/1/4 | 25 | 73 | 9 |
| 11 | 34% H$_3$PO$_4$ on Silica | 2.4 | 230 | 246 | 2/1/4 | 16 | 61 | 17 |

Notes to Table 1
$^a$Based on monoethanolamine and ethylenediamine.
$^b$Mole ratio of ethylenediamine:monoethanolamine:ammonia in the feedstock.
$^c$Results are derived from analyses presented in Table 2, and are rounded off to the nearest integer.
$^d$Based on unchanged monoethanolamine.
$^e$Weight percent of linear and branched polyethylene amines in total polyamine product.
$^f$Weight percent of aminoethylethanolamine (AEEA) in total polyamine product.
$^g$Not evaluated, owing to catalyst failure.

TABLE 2

| Example | PIP[b] | AEP[c] | DETA[d] | TETA(NC)[e] | TETA(C)[f] | TEPA(NC)[g] | TEPA(C)[h] | AEEA[i] |
|---|---|---|---|---|---|---|---|---|
| 1 | 3.26 | 7.04 | 45.28 | 16.35 | 8.83 | 9.68 | 8.54 | 1.02 |
| 2A | 3.01 | 6.02 | 43.10 | 15.42 | 8.69 | 10.85 | 5.06 | 2.00 |
| 2B | 2.62 | 5.61 | 39.48 | 15.39 | 8.67 | 10.49 | 8.62 | 2.67 |
| 2C | 2.63 | 5.35 | 38.08 | 15.03 | 8.74 | 11.95 | 9.11 | 1.98 |
| 2D | 2.89 | 5.58 | 39.98 | 15.86 | 8.01 | 11.19 | 8.13 | 1.79 |
| 2E | 3.14 | 6.08 | 45.42 | 14.87 | 7.81 | 8.87 | 5.85 | 2.39 |
| 2F | 3.43 | 5.41 | 43.44 | 13.86 | 5.96 | 10.47 | 7.41 | 2.00 |
| 3 | 2.38 | 5.03 | 56.61 | 15.53 | 7.85 | 7.24 | 5.36 | 0.0 |
| 4 | 2.44 | 5.32 | 55.69 | 15.77 | 7.95 | 7.57 | 5.26 | 0.0 |
| 5 | 2.37 | 3.56 | 62.14 | 16.18 | 5.50 | 8.09 | 0.97 | 1.19 |
| 6 | 4.00 | 6.83 | 48.44 | 12.75 | 6.65 | 8.02 | 5.93 | 1.86 |
| Comparative 6A | 2.57 | 6.37 | 43.78 | 16.52 | 8.32 | 11.31 | 7.04 | 3.09 |
| Comparative 6B | 2.67 | 5.82 | 42.75 | 15.96 | 7.26 | 11.05 | 5.54 | 5.66 |
| 7 | 3.86 | 6.09 | 48.48 | 13.41 | 4.98 | 9.15 | 4.22 | 4.62 |
| Comparative 7 | 3.16 | 5.65 | 46.97 | 17.00 | 6.08 | 10.58 | 4.11 | 4.67 |
| 8 | 3.52 | 4.71 | 45.99 | 14.80 | 3.56 | 12.37 | 3.03 | 5.07 |
| Comparative 8A | 3.12 | 5.38 | 45.99 | 17.17 | 4.64 | 12.68 | 3.07 | 4.41 |
| Comparative 8B | j | j | j | j | j | j | j | j |
| 9 | 3.93 | 5.83 | 46.60 | 12.71 | 4.30 | 9.38 | 3.27 | 8.49 |
| 10 | 3.61 | 4.90 | 48.41 | 14.16 | 3.23 | 10.69 | 1.65 | 9.07 |
| 11 | 4.28 | 5.02 | 47.70 | 9.92 | 4.61 | 3.56 | 1.53 | 16.76 |

Notes to Table 2
[a]Weight percent of reaction products, expressed on a feedstock-free, water-free, weight-normalized basis.
[b]Piperazine.
[c]Aminoethylpiperazine.
[d]Diethylenetriamine.
[e]Triethylenetetramine (noncyclic isomers).
[f]Triethylenetetramine (cyclic isomers).
[g]Tetraethylenepentamine (noncyclic isomers).
[h]Tetraethylenepentamine (cyclic isomers).
[i]Aminoethylethanolamine.
[j]Not evaluated, owing to catalyst failure.

STATEMENT OF INDUSTRIAL APPLICATION

The inventive process for preparing predominantly noncyclic polyalkylene polyamine compounds is applicable to the preparation of noncyclic polyethylene polyamines which are extensively used in a wide variety of applications. Significant uses of polyethylene polyamines include their use as corrosion inhibitors, fabric softeners, lubricating oil additives, co-monomers for polyamide resins, fungicides, surfactants, curing agents for epoxy resins and chelating agents.

What is claimed is:

1. A process for preparing a noncyclic polyalkylene polyamine which comprises:
   (a) contacting an alkanolamine compound having a primary amino group and a primary or secondary hydroxyl group of the general formula

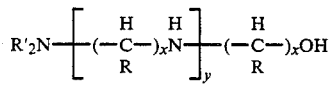

where R is hydrogen or a lower alkyl ($C_1$-$C_4$) radical, x is a number from 2 to 6, and y is a number from 0 to 3, with ammonia and an alkyleneamine compound having two primary amino groups of the general formula:

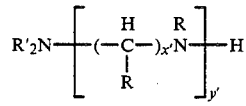

where R is hydrogen or a lower alkyl ($C_1$-$C_4$) radical, x' is a number from 2 to 6, and y' is a number from 1 to 4, in the presence of a catalytically effective amount of a supported phosphoric acid at a temperature from about 210° C. to about 350° C. under a pressure sufficient to maintain a substantial amount of the ammonia in the reaction zone, and
   (b) recovering the noncyclic polyalkylene polyamine from the resultant reaction mixture.

2. The process of claim 1 in which the alkanolamine is monoethanolamine and the ethyleneamine is ethylenediamine.

3. The process of claim 1 wherein the phosphorus-containing substance is phosphoric acid, which is present in an amount from 1 to 85% by weight of said catalyst.

4. The process of claim 3 wherein the liquid hourly space velocity of alkanolamine and alkyleneamine is from about 0.05 to 50.0 hr$^{-1}$.

5. The process of claim 4 wherein the support is comprised of silica, alumina or carbon.

6. The process of claim 4 wherein the level of phosphoric acid supported catalyst is from about 0.1 to 25 mole percent based on alkyleneamine and alkanolamine present in the reaction zone for operation in the liquid phase.

7. The process of claim 6 wherein the mole ratio of alkyleneamine to alkanolamine is from 0:5 to 12:1.

8. The process of claim 6 wherein the mole ratio of alkanolamine to alkyl amine is from 1-2:0.10-20.

9. The process of claim 7 wherein the alkyleneamine is ethylenediamine, the alkanolamine is monoethanolamine, and ammonia is used as reactant.

10. The process of claim 9 in which the alkanolamine is an ethanolamine when R is hydrogen or a lower alkyl ($C_1$–$C_4$) radical, x is 2 and y is 0 to 3, and the alkyleneamine is an ethyleneamine when R is hydrogen or a lower alkyl ($C_1$–$C_4$) radical, x' is 2 and y' is 1 to 4 and the liquid hourly space velocity of alkanolamine and alkyleneamine is from 0.05 to 50 hr.$^{-1}$.

11. The process of claim 10 in which the molar ratio of ethylenediamine:monoethanolamine:ammonia is from 0.75–10:0.5–2:0.10–20.

12. A process for preparing a noncyclic polyalkylene polyamine which comprises:
(a) contacting an alkanolamine compound having an amino group and a primary or secondary hydroxy group of the general formula:

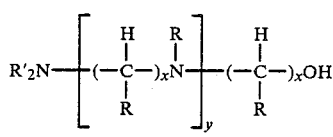

where R is hydrogen or a lower alkyl ($C_1$–$C_4$) radical, R' is hydrogen or an alkyl ($C_1$–$C_{25}$) radical, x is a number from 2 to 6, and y is a number from 0 to 3 with an alkyleneamine compound having two amino groups of the general formula:

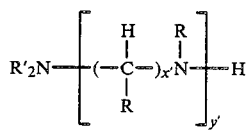

where R is a hydrogen or a lower alkyl ($C_1$–$C_4$) radical, R' is hydrogen or an alkyl ($C_1$–$C_{25}$) radical, x' is a number from 2 to 6, and y' is a number from 1 to 4 and ammonia or an amine of the general formula:

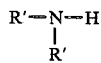

where R' is independently hydrogen or an alkyl ($C_1$–$C_{25}$) radical in the presence of a catalytically effective amount of phosphoric acid on an inert support at a temperature from about 175° C. to about 400° C. under a pressure sufficient to maintain a substantial amount of the ammonia or amine in the reaction zone.

13. A continuous process for preparing predominantly noncyclic polyalkylene polyamines which comprises
(a) adding a charge consisting essentially of ammonia or a primary or secondary amine and an alkanolamine compound having an amino group and a primary or secondary hydroxy group to a reaction zone containing an alkyleneamine compound having two amino groups and a catalytically effective amount of a supported phosphoric acid at a temperature sufficient to effect a reaction among the ammonia or amine, the alkanolamine compound and the alkyleneamine compound under a pressure sufficient to maintain a substantial amount of the ammonia or amine in the reaction zone to produce a reaction product stream comprising ammonia or primary or secondary amine, alkanolamine compound, alkyleneamine compound and polyalkylene polyamines, and
(b) withdrawing the product stream from the reaction zone and separating it to provide a polyalkylene polyamines stream and ammonia or the primary or secondary amine, alkanolamine compound and alkyleneamine compound which are recycled to the reaction zone.

14. The process of claim 12 in which the charge consists essentially of ammonia and monoethanolamine and the alkyleneamine is ethylenediamine.

15. The process of claim 13, in which the molar ratio of ethylenediamine:monoethanolamine:ammonia in the reaction zone is maintained from 0.75–10:0.5–2:0.10–20 and the pressure is from about 5 to 150 atmospheres.

16. In a continuous process for the preparation of predominantly noncyclic polyalkylene polyamine which comprises continuously adding a feed comprising an alkanolamine compound having a primary amino group and a primary or secondary hydroxy group and an alkyleneamine compound having two primary amino groups to a reaction zone containing a catalyst to yield a product stream comprising noncyclic polyalkylene polyamines, alkanolamine compound and alkyleneamine compound, separating the desired polyamines from the product stream and recycling the alkanolamine and alkyleneamine compounds to the reaction zone, the method for substantially reducing the amount of alkyleneamine compound in the feed to the reaction zone, which method comprises
(a) adding ammonia or a primary or secondary alkylamine to the feed to the reaction zone,
(b) using a catalytically effective amount of a supported phosphoric acid as the catalyst, and
(c) effecting the reaction under a pressure from 200–300 psig to maintain a substanial amount of the ammonia or amine in the reaction zone.

17. The method of claim 15 in which unreacted ammonia or amine is recycled to the reaction zone.

18. The method of claim 16 in which the alkanolamine compound is monoethanolamine and the alkyleneamine compound is ethylenediamine.

19. The method of claim 17 in which the temperature is from 175° C. to 400° C.

20. The method of claim 18 in which the pressure is from about 1 to 150 atmospheres.

* * * * *